United States Patent [19]

Röder

[11] Patent Number: 4,807,607
[45] Date of Patent: Feb. 28, 1989

[54] BRACE FOR TREATMENT OF LOWER ARM COMPLAINTS

[76] Inventor: Georg W. Röder, Harksheider Strasse 157, D-2000 Hamburg 65, Fed. Rep. of Germany

[21] Appl. No.: 74,070

[22] Filed: Jul. 16, 1987

[30] Foreign Application Priority Data

Jul. 31, 1986 [DE] Fed. Rep. of Germany ....... 3625983

[51] Int. Cl.⁴ .............................................. A61F 5/00
[52] U.S. Cl. ........................................ 128/77; 128/68
[58] Field of Search .................... 128/77, 80 G, 80 H, 128/68

[56] References Cited

U.S. PATENT DOCUMENTS

| | | | |
|---|---|---|---|
| 3,785,371 | 1/1974 | Lewis | 128/77 |
| 3,934,583 | 1/1976 | Hollingshead et al. | 128/77 |
| 4,182,318 | 1/1980 | Beige et al. | 128/77 |
| 4,313,433 | 2/1982 | Crane | 128/80 H |
| 4,392,487 | 7/1983 | Selner et al. | 128/80 H |
| 4,597,395 | 7/1986 | Barlow et al. | 128/80 H |

FOREIGN PATENT DOCUMENTS

| | | | |
|---|---|---|---|
| 198910 | 10/1965 | Sweden | 128/77 |
| 946529 | 7/1982 | U.S.S.R. | 128/77 |

Primary Examiner—Edgar S. Burr
Assistant Examiner—Tonya Lamb
Attorney, Agent, or Firm—Lane and Aitken

[57] ABSTRACT

A brace made of flexible material has two parts, a collar and a tension brace, which surround the upper and lower arm of a person. Said parts do not hinder blood circulation when the arm is set at an angle, but do exert strong pressure on the bunches of tendons of the lower arm when the muscles are contracted and produce an efficient relief termination for the epicondyles (laterally and medially) when the arm is extended.

15 Claims, 1 Drawing Sheet

U.S. Patent
Feb. 28, 1989
4,807,607
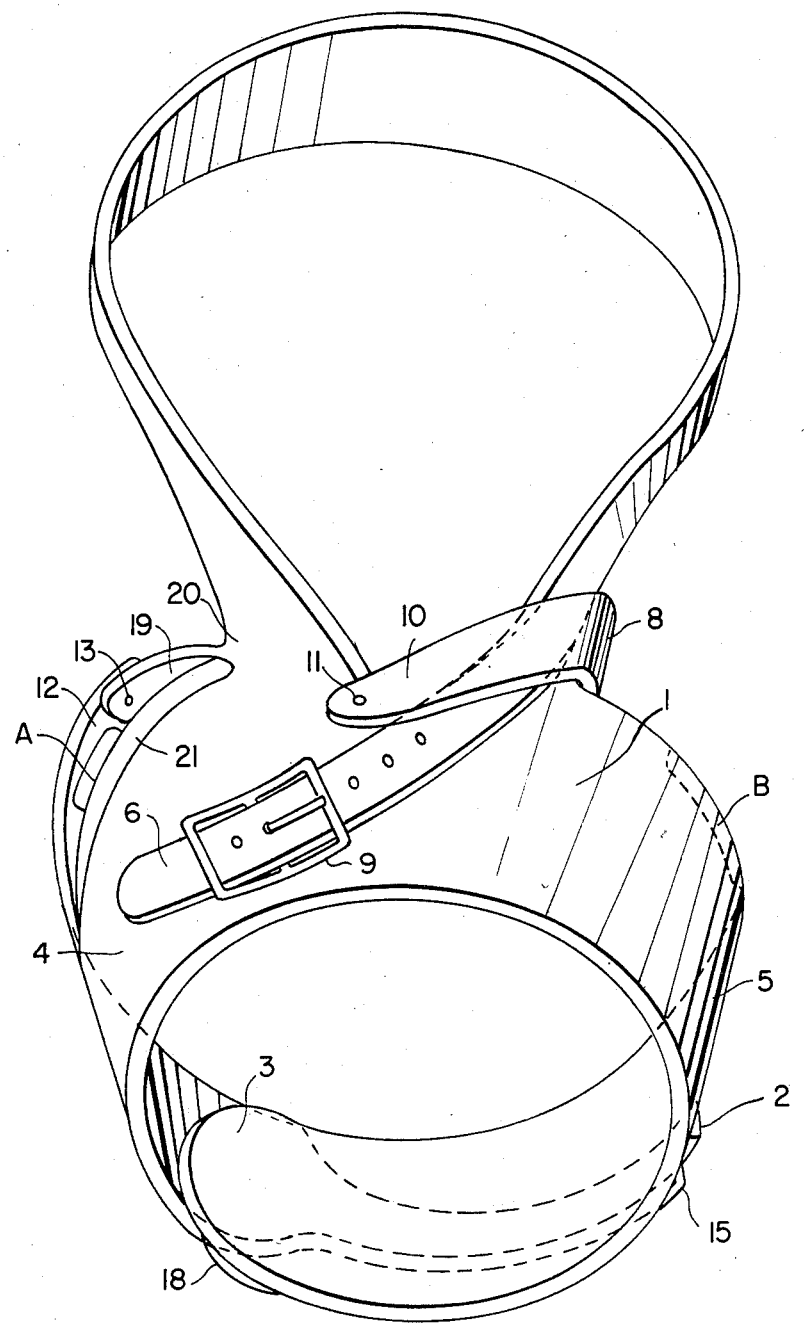

BRACE FOR TREATMENT OF LOWER ARM COMPLAINTS

It is known that complaints and pain in the lower arm which are to be ascribed primarily to frequent tension in the muscles of the lower arm (hence the name tennis arm or tennis elbow) or to monotonous work in an unfavorable position can be alleviated by a brace applied tightly to the lower arm and exerting pressure in the direction of the radius or ulna so that complaints due in particular to epicondylitis or epicondylopathy are mitigated while the brace is worn.

A disadvantage of such braces is that they are effective only if they exert a sufficiently high pressure, that is, are applied so tightly that they necessarily impair circulation of the blood. Hence they may be worn out continuously but only for a brief period during work or while engaging in athletics, as a result of which they scarcely have time to exert their therapeutic effect.

The present invention relates to braces which avoid these disadvantages, and so may be worn for months or years without interruption, and, as experience has already demonstrated, after having been worn for a few months, lead to complete, or at least long-term healing of the tendinous sheaths and of the tendinous insertions.

This is achieved essentially by the special profile imparted to the brace. As a result of this profile, the brace firmly but not tightly encloses the elbow joint and the adjacent parts of the upper and lower arm both when at rest and in movement. This profile does not unduly stress the epicondyles, but does fit so tightly, above all against the critical areas of the tendons when the latter are subjected to noticeable stress, that the direction of tension of the tendons of the musculature of the lower arm is flatter, that is, more nearly tangential to the radius or ulna than would have been the case without the brace, and exerts countertension in the direction of the epicondyles.

The tension brace represents a relief termination for the ends of the tendons, inasmuch as it guides the necessary tension from the forepart of the collar, where the collar is smaller in diameter, to the upper arm. Hence a sleeve such as is claimed for the invention could if desired be designed even in two parts, with the forepart itself providing for tension relief and the portion situated behind it being used to exert pressure on the tendons. One-piece design of the two parts is possible when the force application points for tension relief are situated in front of the areas in which pressure is exerted on the tendons. An embodiment of the invention is preferred in which the two component functions are exerted by a one-piece sleeve, in which case the sleeve itself can be stamped out of a smooth material.

Another characteristic of the brace claimed for the invention may be that it contains two beltlike or collarlike parts joined together by a connecting piece, which parts enclose the areas of the upper and lower arms adjacent to the elbow, and that a cut-out is provided between the parts which leaves the bottom of the elbow free.

Consequently, although the brace claimed for the invention is in two parts, according to a preferred design it consists of a single appropriately shaped piece of a suitable flexible material, preferably genuine or imitation leather, which may be lined with a softer material such as cloth, felt, or the like, and to which only individual attachments such as buckles, climb fasteners, or the like are subsequently added. This preferred embodiment not only offers the production engineering advantage that the brace or its by far the largest and most important part can be stamped out in a single operation, but in addition guarantees especially good interaction of its individual components.

Preferably both the tension brace surrounding the upper arm and the collarlike part enclosing the lower arm are made up of two straps joined to the connecting piece, wound around the upper and lower arm, and joined to each other by means of suitable adjustable connecting means such as climb fasteners or belt buckles of the optimum width for the wearer.

The action exerted by the arrangement claimed for the invention of the two parts joined to each other by a connecting piece, collar and counter-tie, is such that when the arm is subjected to stress, the collar is brought into a position that effects optimum relief and immobilization of the tendinous insertions of both the outer and the inner epicondyle, the tendinous sheath, and simultaneously the elbow and part of the upper arm as well. When effort is exerted, the brace represents a relief termination for the tendinous insertions, while it fits loosely on the arm when the arm is not under stress, the brace claimed for the invention in no way impairing the freedom of movement of the arm; that is, the arm can be fully extended.

The drawing FIG. is a graphic representation of a brace for the right arm.

In the FIG. 2 and 3 denote the end pieces of two straps 4 and 5 which form a collar 1 which can enclose the lower arm of a person. The collar 1 is applied by laying the strap 4 over the strap 5 already wound on the arm and is fixed by fastening means 15 (in the example illustrated, a belt buckle with tongue) in a position in which the tapering collar 1 claimed for the invention rests on and applies pressure precisely to the critical areas A and B of the lower arm (where pads may be situated).

On the upper part of the collar 1 there is a brace attachment 7 which extends from this point into the depth of the figure in the direction of viewing of the drawing and which can be laid around the lower end of the upper arm and which can be adjustably fastened by way of a free end piece 6 to the forepart of the collar by way of a strip attachment 8 with a connection 9.

Parts 7, 8, 6, and 9 represent the essential elements of the present invention; there are no known sleeves having similar or corresponding parts. In any event, these parts are designed so that they can exert tension (forward into the interior of the drawing, in the direction in which the drawing is viewed), so that the collar 1 or its parts 3, 4, and 5 is drawn firmly around the muscular cords of the lower arm when the musculature is subjected to stress.

It is advantageous for the brace attachment 7 or its free end piece to be fixed on the strip attachment 8 by means of a strip 10 fastened on the upper part of the collar 1, which strip 10 is laid over the brace attachment and may be fastened in this position by means of a snap fastener 11. The strip 10 is fastened on the upper part of the collar 1, and can be an integral part of the collar. The strip has a free end which can be lifted over and attached to another point on the brace, where the tension element 7 and the collar 1 meet, so as to define with the collar 1 a slot or loop through which the free end 6 of the tension element 7 can extend on its way to the buckle 9. This structure prevents the buckled end of the tension element from pivoting and sliding clockwise around the collar as viewed in the drawing figure and thereby slipping over the elbow of the wearer under stress.

Another important preferred characteristic of one embodiment of the invention is represented by a strip 12 branching from the upper part of the collar 1, the free end of which strip 12 is connected in the position desired to the bottom of the brace attachment 7 or to a projection of the brace attachment 7. The strip 12 can be connected in the position shown by means of a rivet or snap fastener 13, or may be fastened in openings 19 and 20 in the brace attachment 7. It is essential for the stip 12 to be of a length shorter than would be necessary for reaching the brace attachment 7 with the brace spread out flat. The strip 12 is a part of the collar 1 and diverges from the collar somewhat so that there is a space 21 between the strip 12 and the collar 1. The drawing figure shows the side of the strip 12 which faces the arm of the wearer. Note that the pad at A is shown in solid lines on the strip 12, whereas the pad at B is shown in phantom. The strip 12 is connected to a projecting portion of the tension; element 7 by a fastener 13. Openings 19 and 20 are provided for alternate forms of attachment between the strip 12 and the tension element 7. The free end of the extension from the tension element 7 is shown in solid lines to the left of the fastener 13, whereas the free end of the strip 12 is designated by phantom lines to the right of the fastener 13, thus indicating that the ends of those elements overlap.

As a result of this measure, pressure is exerted on the outer bunches of tendons of the lower arm, as soon as and so long as the thickness of the lower arm is increased by muscular contraction.

According to another design of the invention, an attachment 16 is applied, as by being quilted or glued on, to the exterior of the end piece 3 of the lower strap attachment. The attachment 16 is secured to the exterior of the end piece 3 from which it extends toward and beyond the other end of the collar so that the other end of the collar rests on the attachment. The other lower strap 4 can rest on this attachment 16, this guaranteeing shaping marked by permanent proper fit. Particularly in conjunction with the mode of application already described (shaping of the collar first), this embodiment offers the advantage that, once a well fitting collar 1 and the tension brace 7 have been formed, they need never be opened again but retain their shape even when removed and put on again.

For the purpose of removal or repositioning of the collar 1, the opening in the latter is enlarged by lifting the strap 4 from the attachment 16. Positioning or removal of the tension brace 7 is also made possible or easier without opening the brace in that, after the snap fastener 11 has been opened, the strip 10 releases the tension brace 7 and the latter can be slid over the elbow.

I claim:

1. A brace for treatment of complaints caused by overstressing of the tendinous insertions and/or the tendon sheath of the lower arm comprising:

a collar positionable around the lower arm, said collar defining an exterior side and an interior side;

at least one pad on the interior side of said collar for engagement with the lower arm;

a tension element connected to said collar and postionable around the upper arm, said tension element having a free end;

means for fastening said free end of said tension element to said collar, said brace being made from a flexible material; and a strip branching from the upper edge of the collar and leading to the tension element, said strip having an end connected with the tension element, whereby the brace exerts pressure on bunches of tendons of the lower arm when muscles of the lower arm contracted and provides relief for ends of tendons of the lower arm by transmitting the tension from the collar through the tension element to the upper arm.

2. A brace as claimed in claim 1, wherein the length of the strip (12) is shorter than is necessary for reaching the tension element (7) when the brace is extended so as to be completely flat.

3. A brace as claimed in claim 1, wherein said fastening mans is a climb fastener.

4. A brace as claimed in claim 1, wherein said fastening means is a belt buckle with a tongue.

5. A brace as claimed in claim 1, wherein the fastening means (11) is a snap fastener.

6. A brace as claimed in claim 1, wherein said material comprises lined or unlined leather, textile fabric, formed fabric, or plastic.

7. A brace as claimed in claim 1, further comprising a strip fastened on said collar, said strip having a free end, the free end of said strip being fastened to said collar adjacent to the connection of said tension element to said collar, whereby said strip forms with said collar a loop through which the free end of said tension element may extend.

8. A brace as claimed in claim 1, wherein said collar and said tension element are made from the same piece of said flexible material.

9. A brace as claimed in claim 1, wherein a fastener (13) is used to connect the end of the strip (12) with the tension element (7).

10. A brace as claimed in claim 9, wherein the fastener is a rivet.

11. A brace as claimed in claim 9, wherein the fastener is a snap fastener.

12. A brace as claimed in claim 1, wherein said collar includes a first end and a second end and means for securing said first end to said second end.

13. A brace as claimed in claim 12, wherein said securing means is a climb fastener.

14. A brace as claimed in claim 12, wherein said securing means is a belt buckle with a tongue.

15. A brace as claimed in claim 12, wherein said first end of said collar overlaps said second end, and there is an attachment mounted on the exterior of one of the first and second ends, the other of said first and second ends resting on said attachment.

* * * * *